United States Patent

Horrigan et al.

[11] Patent Number: 5,388,590
[45] Date of Patent: Feb. 14, 1995

[54] CATHETER EXCHANGE DEVICE

[75] Inventors: John B. Horrigan, Merrimack; Peter A. Lunn, Beverly; David S. Brin, West Newbury, all of Mass.

[73] Assignee: Medtronic, Inc., Minneapolis, Minn.

[21] Appl. No.: 98,185

[22] Filed: Jul. 28, 1993

[51] Int. Cl.⁶ .................................. A61B 5/00
[52] U.S. Cl. ............................. 128/772; 128/658
[58] Field of Search ............ 128/657, 658, 772; 604/95, 280–283

[56]  References Cited

U.S. PATENT DOCUMENTS

| 5,046,497 | 9/1991 | Millar | 128/537 |
| 5,131,407 | 7/1992 | Ischinger et al. | 128/772 |
| 5,167,239 | 12/1992 | Cohen et al. | 128/772 |

FOREIGN PATENT DOCUMENTS

| 2022861 | 7/1989 | Canada . |
| 2024060 | 2/1991 | Canada . |
| 0416734 | 7/1990 | European Pat. Off. . |
| 0415332 | 8/1990 | European Pat. Off. . |

Primary Examiner—Max Hindenburg
Attorney, Agent, or Firm—Dianne Plunkett; Harold R. Patton

[57] ABSTRACT

The invention includes an exchange system, a guidewire anchoring means and a method of use for catheters exchangeable over a guidewire (55). The guidewire anchoring means restricts movement between the guidewire (55) and the anchoring means. The anchoring means comprises a shaft (35) with a longitudinal lumen (80) therethrough, the lumen (80) being in fluid communication with a balloon (25 or 30) disposed on the distal end of the shaft (35). A tubular split housing (5 or 10) surrounds the distal end of the shaft (35) and adheres to the balloon (25 or 30), the balloon (25 or 30) being sized to expand to a larger size than the inside diameter of the split housing (5 or 10). The inside diameter of the split housing (5 or 10) is sized to slidably receive a catheter, while the outside diameter of the split housing (5 or 10) is sized to slidably fit within a guide catheter (50).

21 Claims, 4 Drawing Sheets

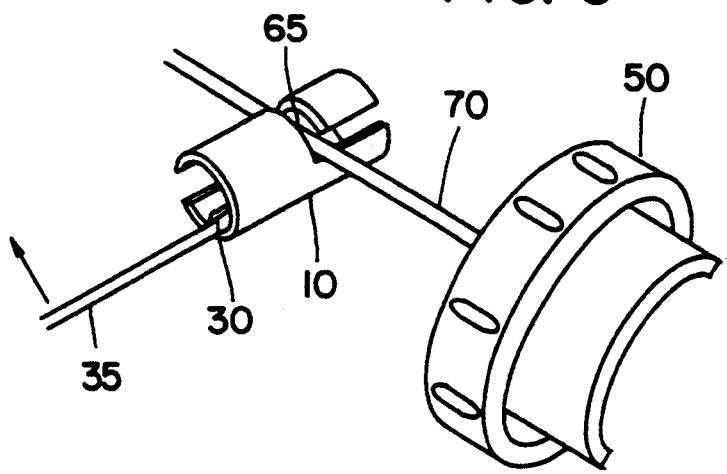
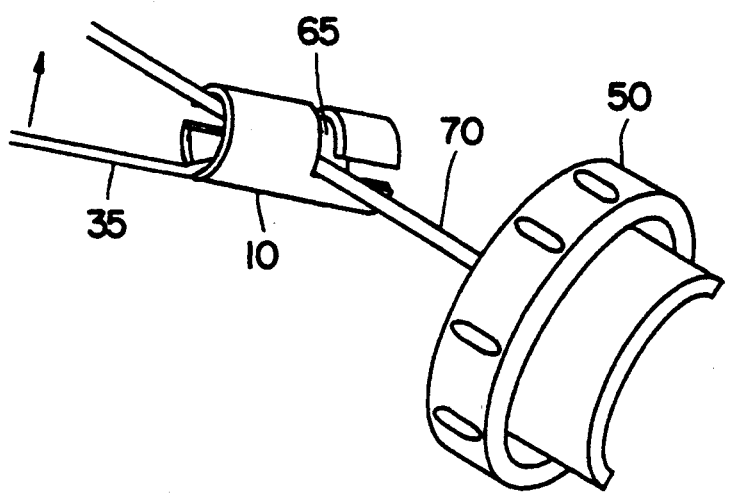
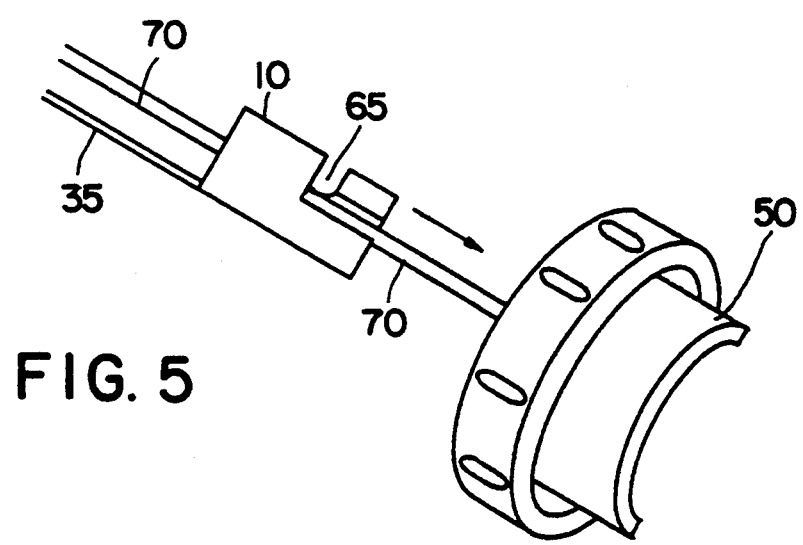

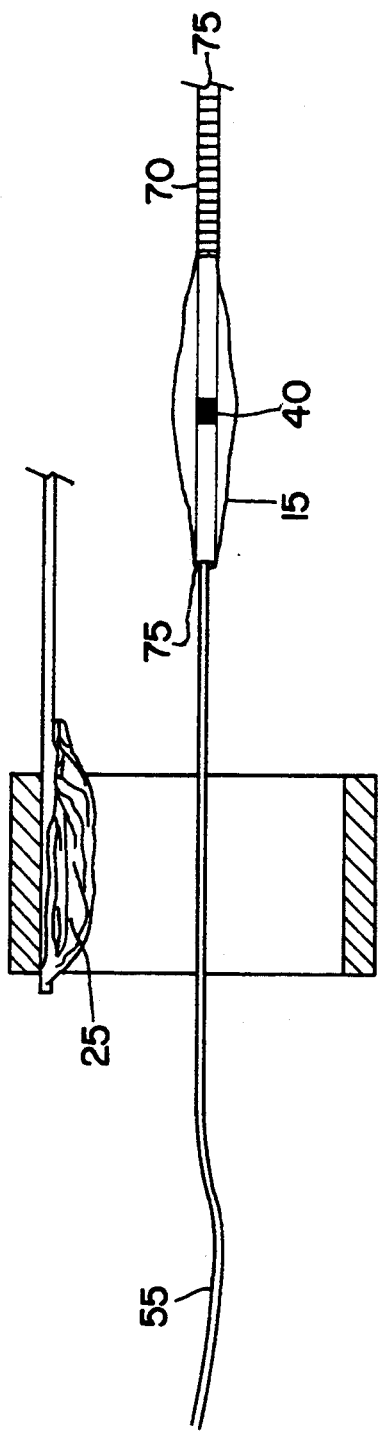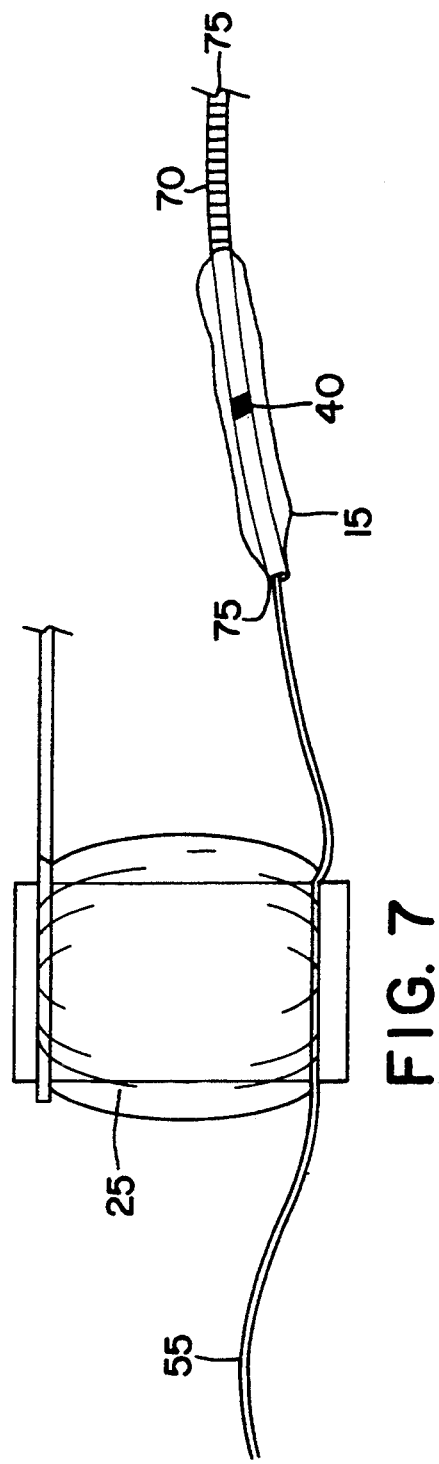

CATHETER EXCHANGE DEVICE

FIELD OF THE INVENTION

The present invention relates to catheters, and more particularly, to a device for holding a guidewire in place while exchanging a catheter of one size for one of another size.

BACKGROUND OF THE INVENTION

Catheters are tube-like members inserted into the body for diagnostic or therapeutic reasons. One of the therapeutic procedures applicable to the present invention is known as percutaneous transluminal coronary angioplasty (PTCA). This procedure can be used, for example, to reduce arterial build-up of cholesterol fats or atherosclerotic plaque.

An over-the-wire catheter is characterized by a free central lumen through which a movable guidewire can be passed. Once the stenosis is located with the guidewire, a dilatation balloon catheter is advanced over a 150 cm guidewire to the stenosis location. Using such a movable wire system, one could more readily select the desired coronary artery and reach smaller branches as movable guidewires are smaller and more flexible than the fixed wire systems. Over-the-wire systems are disadvantageous because 150 cm of guidewire must be maintained outside the body either by an extension wire or by a 300 cm long guidewire. This length of guidewire is difficult to handle because it requires two operators who must be in communication during the procedure. This requires more time and risks contamination by dropping the guidewire from the sterile field. Furthermore, extension wires require additional time to assemble and their connecting parts may prevent smooth exchanges. Over-the wire systems are disadvantageous if a catheter must be exchanged for one of a different size because during the process of removing the first catheter, the guidewire may become dislodged from the stenosis resulting in the need to relocate the stenosis upon insertion of the subsequent catheter.

To respond to the disadvantage of inadvertently moving the guidewire during the exchange procedure, several methods of trapping the guidewire and holding it stationary during the exchange have been developed. One method involves a balloon built into the distal end of the catheter wall which fills the lumen around the guidewire thereby holding it stationary. A second method consists of an inflatable balloon disposed on a guidewire. Yet another method involves an accessory device which tracks the guidewire beyond the stenosis where it is deployed about the guidewire thereby holding the guidewire stationary during the exchange. Applicant's invention represents the tracking type of device.

U.S. Pat. No. 5,046,497 to Millar for "Structure for Coupling a Guide Wire and Catheter" discloses a device having a coupling structure comprising a pair of spaced-apart fingers adapted for receiving a guidewire. A guidewire is inserted through the guiding catheter. Multiple devices may be coupled to the guidewire and tracked down the guidewire and positioned in the region of interest.

U.S Pat. No. 5,131,407 to Ischinger et al for "Guide Wire with Tracking Member and Catheter Exchange System" discloses a guidewire with a helical coil surrounding the smaller diameter spring coil on the guidewire at the distal end for tracking a catheter. With the guidewire positioned in the stenosis, the catheter can be exchanged. The helically coiled tracking member can be withdrawn into the guidewire by pulling on the proximal end of the pull wire. After the guidewire has been advanced and its distal end positioned in the stenosis, and after the previous catheter has been withdrawn, a guidewire extension is attached to the proximal end of the guidewire in order that some portion of the guidewire will be exposed as the succeeding catheter is advanced over the guidewire.

U.S Pat. No. 5,167,239 to Cohen et al for an "Anchorable Guide Wire" discloses a guidewire with an inflatable balloon disposed on the distal end to anchor the guidewire in a fixed position while catheters, scopes or other instruments are advanced/retracted over the proximal end and/or body of the guidewire.

European Patent Application Publication No. 415,332 A1 and Canadian Patent Application No. A1 2,024,060 to Keith et al for "Method and Apparatus for Catheter Exchange by Guide Wire Captivation" discloses a means for selectively engaging the guidewire within the guide catheter to restrict longitudinal movement of the guidewire relative to the guide catheter. One embodiment comprises a guidewire captivation catheter and a dilatation catheter which are inserted into a guide catheter. The captivation catheter's uninflated balloon is positioned distally of the dilatation catheter's balloon. Inflating the captivation catheter's balloon pushes the dilatation catheter's guidewire against an inner wall of the guide catheter thus holding it stationary. Once inflated, however, the guide catheter lumen is obstructed thus precluding blood pressure monitoring. The physician is also precluded from injecting contrast through the guide catheter and looses the ability to move or manipulate the guidewire during the exchange. When the captivation catheter's balloon is withdrawn, a static column of blood can be created and introduce air. In the second embodiment, an inflation lumen is formed in the wall of the guide catheter between an inner wall surface and an outer wall surface at the distal end of the guide catheter. Such a design reduces the size on the guide catheter inflation lumen. Once inflated the guidewire is immobilized. The guide catheter lumen, however, is obstructed thus precluding blood pressure monitoring. In the second embodiment, the exchange balloon is a standard feature which the user pays for whether it is used or not.

European Patent Application Publication No. 416,734 A1 and Canadian Patent Application No. A1 2,022,861 to Coehlo for "Guide Catheter and Guide Wires for Effecting Rapid Catheter Exchange" discloses a guide catheter and a guidewire, one of which carries a mechanism for gripping the other during exchange of catheters over the guidewire. In one embodiment, the mechanism is an inflatable balloon on the distal end of the guide catheter. When inflated, the balloon frictionally grips the guidewire to immobilize it. In another embodiment, the mechanism is an inflatable balloon disposed on a guidewire. Once inflated, the guide catheter lumen is obstructed thus precluding blood pressure monitoring in either embodiment. The physician is also precluded from injecting contrast through the guide catheter and loses the ability to move or manipulate the guidewire during the exchange. When the captivation guidewire's balloon is withdrawn, a static column of blood can be created and introduce air. In either embodiment, the exchange balloon is a standard feature which the user pays for whether it is used or not.

What is needed is a device that facilitates the exchange of catheters without requiring the inner wall of the guide catheter to secure the guidewire, so that fluids can pass through the guide catheter while the device is securing the guidewire. The physician should also be able to move the guidewire during the exchange if desired. The device should allow any over-the-wire catheter as for example, a dilatation balloon catheter to be exchanged over any standard length guidewire without extending the guidewire or occluding the lumen of the guide catheter.

SUMMARY OF THE INVENTION

The present invention is implemented in three aspects, a catheter system, a method of use and a guidewire anchoring means. Applicant's invention provides an exchange device for catheters exchangeable over a guidewire by having a guidewire anchoring means to restrict movement between the guidewire and the anchoring means. Applicant's anchoring means tracks over the guidewire and catheter to the a location distal to the catheter and then maintains the guidewire in place over the area to be treated while catheters are exchanged over the guidewire. The anchoring means comprises a shaft with a longitudinal lumen therethrough, the lumen being in fluid communication with a balloon disposed on the distal end of the shaft. A tubular split housing surrounds the distal end of the shaft and adheres to the balloon which is sized to expand to a size larger than the inside diameter of the split housing. The inside diameter of the split housing is sized to slidably receive a catheter, while the outside diameter of the split housing is sized to slidably fit within a guide catheter. The split in the housing has opposed sides which are sufficiently flexible to allow the guidewire to be pressed through the split for loading, yet fit tightly enough to preclude the guidewire from being released during the medical procedure.

In one embodiment, the "split ring housing," the split in the housing is cut on an angle to the longitudinal axis of the housing. In another embodiment, the "opposed split housing," an opposed split begins parallel to the housing longitudinal axis and is cut from the proximal end of the housing to the midpoint of the housing then continues perpendicular to the longitudinal axis over to the opposite side of the housing. From that point the slot becomes parallel to the housing's longitudinal axis and extends from the housing midpoint to the distal end of the housing.

The advantages of applicant's invention are that it facilitates the exchange of catheters without requiring the inner wall of the guide catheter to secure the guidewire so that fluids can pass through the guide catheter while the device is securing the guidewire. With fluid flow, pressures can be monitored and contrast can be injected, for example. The physician can also control the guidewire while withdrawing the balloon from the guide catheter. The device allows any over-the-wire catheter to be exchanged over any standard length guidewire without extending the guidewire or occluding the lumen of the guide catheter.

BRIEF DESCRIPTION OF THE DRAWINGS

FIGS. 3–5 show the opposed split housing being positioned over a dilatation balloon;

FIGS. 6–7 show the split ring housing's balloon being inflated to secure the dilatation catheter's guidewire;

DETAILED DESCRIPTION OF THE PREFERRED EMBODIMENTS

Figure 1:
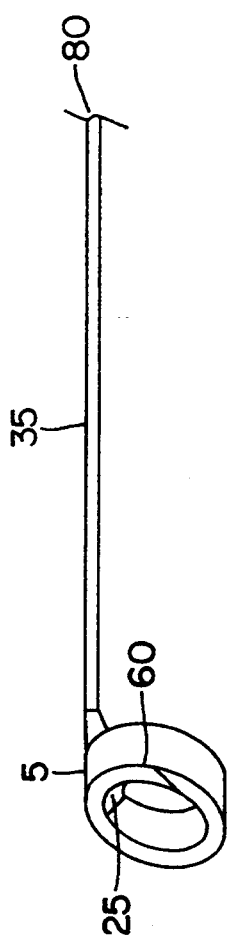
FIG. 1 is the perspective view of the split ring housing.
Figure 2:
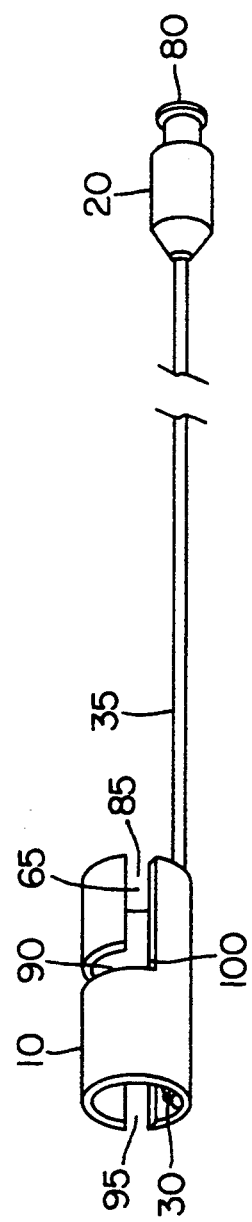
FIG. 2 is the perspective view of the opposed split housing.

FIG. 1 represents a split ring housing while FIG. 2 represents the opposed split housing. The proximal end of the two embodiments are similarly constructed. That is, the luer fitting 20, distal end is attached to the proximal end of a shaft 35 which is a semi-rigid inflation lumen 80 of approximately 100 cm in length. The shaft 35 is in fluid communication with a balloon 25 or 30. The shaft can be made of biocompatible materials such as rigid polymers or flexible metals.

In FIG. 1, balloon 25 is adhered to the inside wall of the split ring housing 5. In FIG. 2, balloon 30 is adhered to the inside wall of the opposed split housing 10. Balloon 25 and 30 are sized such that when inflated, they expand to a size slightly larger than the inside diameter of the split ring housing 5 or opposed split housing 10 respectively. Balloons 25 and 30 are made of biocompatible material such as low density polyethylene. Balloons 25 and 30 can be attached to the housing with adhesive bonding preferably or by heat bonding. When bonded, two mating surfaces are filled with adhesive as for example, cyanoacrylate or epoxy. Split ring housing 5 and opposed split housing 10 are made of biocompatible materials such as rigid plastics. The preferred length of the split ring housing 5 or of the opposed split housing 10 is 0.250 inches or 0.635 cm. The preferred inner diameter of the split ring housing 5 or of the opposed split housing 10 is 0.055 inches or 0.14 cm. The preferred outer diameter of the split ring housing 5 or of the opposed split housing 10 is 0.065 inches or 0.165 cm.

The FIG. 1 split ring housing 5 is formed of a tubular member which has a slit 60 which lies on an angle of approximately 35–55 degrees and more preferably a 45 degree angle to the longitudinal axis of the housing 5 through which the catheter 70 can be inserted. The opposing sides of the split ring housing 5 on either side of the slit 60 fit tightly enough that the catheter 70 or guidewire 55 will not be released during the medical procedure yet are flexible enough and wide enough to permit the catheter 70 to be pressed through the slit 60 during loading.

The FIG. 2 opposed split housing 10 is formed from a tubular member and has an opposed split 65 through which the catheter 70 can be pressed. The opposing sides of the housing 10 on either side of the opposed split 65 fit tightly enough that the catheter 70 or guidewire 55 will not be released during the medical procedure yet are flexible enough and wide enough to permit the catheter 70 to be pressed through it for loading. The opposed split 65 is formed as follows. A first segment 85 of approximately 0.010 inches or 0.025 cm wide begins parallel to the housing 10 longitudinal axis and is cut from the proximal end of housing 10 to approximately the midpoint 100 of housing 10. The second segment 90 then continues perpendicular to the longitudinal axis and extends to the opposite side of housing 10 with a split width of 0.050 inches or 0.127 cm. From that point the third segment 95 is parallel to the housing 10 longitudinal axis and extends to the distal end of housing 10 with a split width of approximately 0.010 inches or 0.025 cm.

Figure 8:
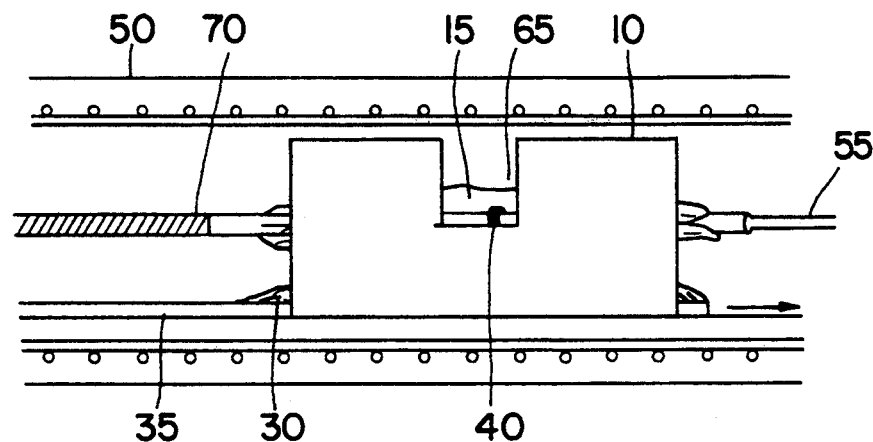
FIGS. 8–9 show the opposed split housing's balloon being inflated to secure the dilatation catheter's guidewire.
Figure 9:
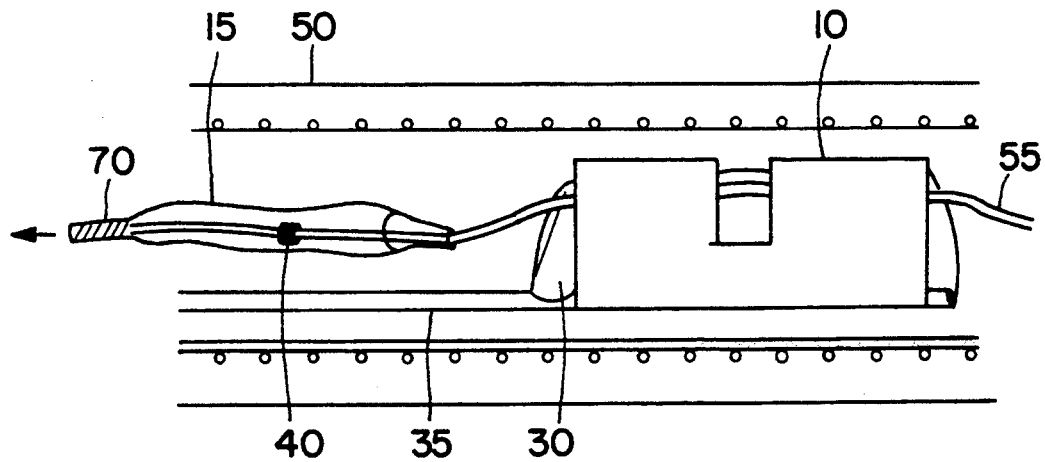
Figure 10:
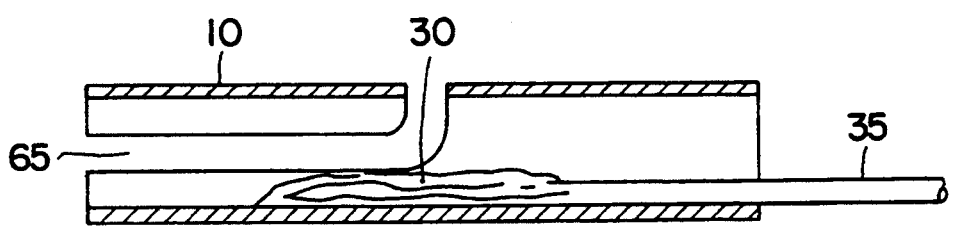
FIG. 10 shows a longitudinal cross section of the distal end of the opposed split housing.

Procedurally, the guide catheter 50 is positioned at the treatment site, for example, in a coronary artery. The guidewire 55 is then positioned distal to the guide catheter 50 and across the lesion. The proximal end of the guidewire 55 is backloaded into the distal end of a catheter lumen 75, as for example, a balloon dilatation catheter 70, and the catheter advanced to the site of the lesion where the dilatation balloon 15 is inflated. Other catheters could be used such as diagnostic catheters or atherectomy devices. If a different sized balloon dilatation catheter 70 or a different type of catheter is required, the dilatation balloon 15 is deflated, then the opposed split ring housing 10 is snapped over the catheter 70 (See FIGS. 3–5) and advanced into the guide catheter 50 by tracking over the guidewire 55 and down the balloon dilatation catheter 70 to a location distal to the balloon dilatation catheter 70 with the housing over the guidewire 55. The opposed split housing balloon 30 is then inflated (See FIGS. 8–9). The same procedure could also use the split ring housing 5 by instead inflating the split ring housing balloon 25. The inflated device now secures the guidewire 55 against the inside surface of the housing without the use of the guide catheter 50. The first balloon dilatation catheter 70 can now be removed and be replaced by one of a different size by backloading it onto the proximal end of the guidewire 55 and advancing it down the guide catheter 50 until its forward movement is stopped by the inflated housing balloon 25 or 30. The housing balloon is then deflated and housing 5 or 10 removed from the guide catheter 50. The second catheter can then be advanced to the desired site.

The advantages of the invention are that it facilitates the exchange of catheters without requiring the inner wall of the guide catheter 50 to secure the guidewire 55 so that fluids can pass through the guide catheter 50 while the device is securing the guidewire 55. With fluid flow, pressures can be monitored and contrast can be injected, for example. The physician can also control the guidewire 55 while withdrawing the catheter 70 from the guide catheter 50. The device allows any over-the-wire catheter 70 to be exchanged over any standard length guidewire 55 without extending the guidewire 55 or occluding the lumen of the guide catheter 50.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
| --- | --- |
| 5 | Split Ring Housing |
| 10 | Opposed Split Housing |
| 15 | Dilatation Balloon |
| 20 | Luer Fitting |
| 25 | Split Ring Housing Balloon |
| 30 | Opposed Split Housing Balloon |
| 35 | Shaft |
| 40 | Radiopaque Marker Band |
| 45 | Distal Tip |
| 50 | Guide Catheter |
| 55 | Guidewire |

-continued

| No. | Component |
| --- | --- |
| 60 | Slit |
| 65 | Opposed Split |
| 70 | Balloon Dilatation Catheter |
| 75 | Catheter Lumen |
| 80 | Shaft Lumen |
| 85 | First Segment |
| 90 | Second Segment |
| 95 | Third Segment |
| 100 | Midpoint |

What is claimed is:

1. A catheter system comprising:
   (a) a guidewire;
   (b) a catheter having a lumen adapted to slidably receive the guidewire through the lumen; and
   (c) a guidewire anchoring means to restrict movement between the guidewire and the anchoring means, the anchoring means comprising:
      (i) a balloon;
      (ii) a shaft having a distal end and a proximal end;
      (iii) a longitudinal lumen throughout the shaft having the lumen being in fluid communication with the balloon, the balloon being disposed on the distal end of the shaft;
      (iv) a tubular split housing with a distal end and a proximal end, the housing having an inside diameter, the housing surrounding the distal end of the shaft, the balloon being adhered to the inside diameter of the housing, the balloon being sized to expand to a larger size than the inside diameter of the split housing, the inside diameter of the split housing being sized to slidably receive a catheter.

2. The catheter system of claim 1 wherein the housing is about 0.635 cm in length, with an outer diameter of about 0.165 cm and an inner diameter of about 0.14 cm.

3. The catheter system of claim 1 wherein the shaft is about 100 cm in length.

4. The catheter system of claim 1 wherein the balloon is disposed on the shaft and adhered to the housing using adhesive such as cyanoacrylate or epoxy and wherein the balloon is comprised of a biocompatible material including low density polyethylene.

5. The catheter system of claim 1 further comprising a split ring housing with a longitudinal slit in the housing, the slit being cut on an angle to the housing longitudinal axis and permitting the insertion of the catheter.

6. The catheter system of claim 5 wherein the slit has an angle with a range of approximately 35–55 degrees relative to the housing longitudinal axis and wherein the slit is at an angle of 45 degrees relative to the housing longitudinal axis.

7. The catheter system of claim 1 further comprising the housing having an opposed split, the split having, in order from the housing proximal end, a first segment, a second segment, and a third segment, the split permitting the insertion of a catheter.

8. The catheter system of claim 7 wherein the split of the first segment is made with a cut approximately 0.025 cm wide parallel to the longitudinal axis of the housing, the split of the first segment originating at the proximal end of the housing and running to approximately the midpoint of the housing.

9. The catheter system of claim 7 wherein the split of the second segment is made with a cut of approximately 0.127 cm wide running perpendicular to the housing longitudinal axis, from the midpoint to the opposite side of the opposed split housing.

10. The catheter system of claim 7 wherein the split of the third segment runs parallel to the housing longitudinal axis from the distal end of the second segment and continues to the distal end of the opposed split housing, the third segment having a width of approximately 0.025 cm.

11. A method of exchanging catheters over a guidewire comprising the steps of:
 (a) providing a guidewire, a first catheter, a second catheter, and a guidewire anchoring means, the guidewire anchoring means having a shaft, a housing and a balloon, the shaft having a lumen therethrough, the lumen being in fluid communication with the balloon, the housing having a split therethrough, the housing having an inside diameter and the balloon being disposed upon the inside diameter of the housing;
 (b) advancing the guidewire to the desired location;
 (c) advancing a first catheter over the proximal end of the guidewire to the desired location;
 (d) pressing the proximal end of the first catheter through the split in the housing;
 (e) advancing the guidewire anchoring means over the first catheter past the distal end of the first catheter and over the guidewire;
 (f) inflating the balloon to a size that inhibits movement of the guidewire within the split housing;
 (g) withdrawing the first catheter from the body while leaving the guidewire anchoring means in place;
 (h) advancing the second catheter over the guidewire to the housing;
 (i) deflating the balloon;
 (j) withdrawing the guidewire anchoring means over the second catheter.

12. A guidewire anchoring means comprising:
 (a) a balloon;
 (b) a shaft having a distal end and a proximal end;
 (c) the shaft having a longitudinal lumen therethrough, the lumen being in fluid communication with the balloon, the balloon being disposed on the distal end of the shaft;
 (d) a tubular split housing with a distal end and a proximal end, the housing having an inside diameter, the housing surrounding the distal end of the shaft the balloon being adhered to the inside diameter of the housing, the balloon being sized to expand to a larger size than the inside diameter of the split housing, the inside diameter of the split housing being sized to slidably receive a catheter.

13. The guidewire anchoring means of claim 12 wherein the housing is about 0.635 cm in length, with an outer diameter of about 0.165 cm and an inner diameter of about 0.14 cm.

14. The guidewire anchoring means of claim 12 wherein the shaft is preferably 100 cm in length.

15. The guidewire anchoring means of claim 12 wherein the balloon is disposed on the shaft and adhered to the housing using adhesive such as cyanoacrylate or epoxy and wherein the balloon is comprised of a biocompatible material including low density polyethylene.

16. The guidewire anchoring means of claim 12 further comprising a split ring housing with a longitudinal split in the housing, the split being cut on an angle to the housing longitudinal axis and permitting the insertion of the catheter.

17. The guidewire anchoring means of claim 16 wherein the slit has an angle with a range of approximately 35–55 degrees relative to the housing longitudinal axis and wherein the slit is at an angle of 45 degrees relative to the housing longitudinal axis.

18. The guidewire anchoring means of claim 12 further comprising the housing having an opposed split, the split having, in order from the housing proximal end, a first segment, a second segment, and a third segment, the split permitting the insertion of a catheter.

19. The guidewire anchoring means of claim 18 wherein the split of the first segment is made with a cut approximately 0.025 cm wide parallel to the longitudinal axis of the housing, the split of the first segment originating at the proximal end of the housing and running to approximately the midpoint of the housing.

20. The guidewire anchoring means of claim 18 wherein the split of the second segment is made with a cut of approximately 0.127 cm wide running perpendicular to the housing longitudinal axis, from the midpoint to the opposite side of the housing.

21. The guidewire anchoring means of claim 18 wherein the split of the third segment runs parallel to the housing longitudinal axis from the distal end of the second segment and continues to the distal end of the housing, the third segment having a width of approximately 0.025 cm.

* * * * *